US 6,735,272 B1

(12) United States Patent
Sorenson

(10) Patent No.: US 6,735,272 B1
(45) Date of Patent: May 11, 2004

(54) METHOD AND SYSTEM FOR A CUSTOMIZED PATIENT REPORT IN IMAGING SYSTEMS

(75) Inventor: Jeffrey Sorenson, Sussex, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 41 days.

(21) Appl. No.: 10/065,449

(22) Filed: Oct. 18, 2002

(51) Int. Cl.⁷ .............................. A61B 6/03; A61B 6/04
(52) U.S. Cl. ................... 378/4; 378/37; 378/62
(58) Field of Search .............. 378/4, 37, 62, 378/98, 901

(56) References Cited

U.S. PATENT DOCUMENTS

| | | | | |
|---|---|---|---|---|
| 4,591,974 A | * | 5/1986 | Dornbush et al. | ........... 715/509 |
| 5,636,920 A | | 6/1997 | Shur et al. | ........... 364/410 |
| 5,920,871 A | * | 7/1999 | Macri et al. | ........... 707/104.1 |
| 6,243,437 B1 | | 6/2001 | Hu et al. | ........... 378/8 |
| 2002/0040282 A1 | * | 4/2002 | Bailey et al. | ........... 702/188 |

FOREIGN PATENT DOCUMENTS

| | | |
|---|---|---|
| EP | 1 160 716 A2 | 5/2001 |
| WO | WO 01/13276 A1 | 2/2001 |

* cited by examiner

*Primary Examiner*—David V. Bruce
(74) *Attorney, Agent, or Firm*—Cantor Colburn LLP

(57) ABSTRACT

A method and system for associating medical imaging data with a customized patient report. The system includes a memory for storing a plurality of patient specific attributes and a plurality of user defined rules, the attributes include patient specific medical image data. A stored program is configured to apply a rule to a corresponding attribute and allow an end user to at least one of create, edit, and add at least one of the attributes and the user defined rules. A processor operates with the stored program for processing to establish a conclusion to the rule. An output device is included and configured to generate the customized patient report having the conclusion in text format. The text in the conclusion is also end user configurable.

31 Claims, 4 Drawing Sheets

METHOD AND SYSTEM FOR A CUSTOMIZED PATIENT REPORT IN IMAGING SYSTEMS

BACKGROUND OF INVENTION

The present invention relates generally to the field of medical diagnostic systems, such as imaging systems of various modalities. More particularly, the invention relates to a technique for providing patient data and reports in conjunction with such diagnostic systems.

This section is intended to introduce the reader to various aspects of art which may be related to various aspects of the present invention which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Medical diagnostic and imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, and so forth. In many instances, these modalities complement one another and offer the physician a range of techniques for imaging particular types of tissue, organs, physiological systems, and so forth. Health care institutions often dispose several such imaging systems at a single facility or at multiple facilities, permitting its physicians to draw upon such resources as required by particular patient needs.

Modern medical diagnostic systems typically include circuitry for acquiring image data and for transforming the data into a useable form, which is then processed to create a reconstructed image of features of interest within the patient. The image data acquisition and processing circuitry is often referred to as a "scanner" regardless of the modality, because some sort of physical or electronic scanning often occurs in the imaging process. The particular components of the system and related circuitry, of course, differ greatly between modalities due to their different physics and data processing requirements.

Medical diagnostic systems of the type described above are often called upon to produce reliable and understandable images with a corresponding patient report. While such images and patient reports have proven extremely valuable in diagnostic systems, further improvements are still needed. For example, to detect coronary calcification in a patient, computer tomography (CT) images of the patient's heart are generated and reviewed to identify calcium deposits. In one type of diagnostic system, the CT screening application involves a patient report, which details out the study results. This may include a percentile value, which details which risk category the patient belongs to in a population. Current calcium-scoring packages currently list out only a calcium score and a percentile value dependent on the age and gender of the patient. However, calcium score is only one of the many factors, which go into the assessment of cardiovascular disease (CVD) risk.

While this information is useful in assessment of CVD, there is a need to provide the physician the capability to create a customized diagnostic message based on other factors such as cholesterol, exercise levels, blood pressure etc. Thus, there is a particular need to present the patient with a customized diagnostic message, which is created by considering all of the patient factors and their interplay based on current diagnostic and operational data and further provides historical data for comparative purposes.

SUMMARY OF INVENTION

The above discussed and other drawbacks and deficiencies are overcome or alleviated by a method and system for associating medical imaging data with a customized patient report. The system includes a memory for storing a plurality of patient specific attributes and a plurality of user defined rules, the attributes include patient specific medical image data. A stored program is configured to apply a rule to a corresponding attribute and allow an end user to at least one of create, edit, and add at least one of the attributes and the user defined rules. A processor operates with the stored program for processing to establish a conclusion to the rule. An output device is included and configured to generate the customized patient report having the conclusion in text format. The text in the conclusion is end user configurable, as well as the attributes and rules.

The method includes storing a plurality of patient specific attributes and a plurality of rules; the attributes include patient specific medical image data. The method further includes configuring a stored program to apply a rule to corresponding attributes, and configuring the stored program to allow an end user to at least one of create, edit, and add at least one of the attributes and defined rules. The method also includes processing the rule to establish a conclusion to the rule and configuring an output device to generate the customized patient report having the conclusion in text format. The method allows the conclusion, as well as the attributes and rules, to be end user configurable.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Additionally, used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features. Also as used herein, the phrase "reconstructing an image" is not intended to exclude embodiments of the present invention in which data representing an image is generated but a viewable image is not. However, many embodiments generate (or are configured to generate) a viewable image.

Figure 1:
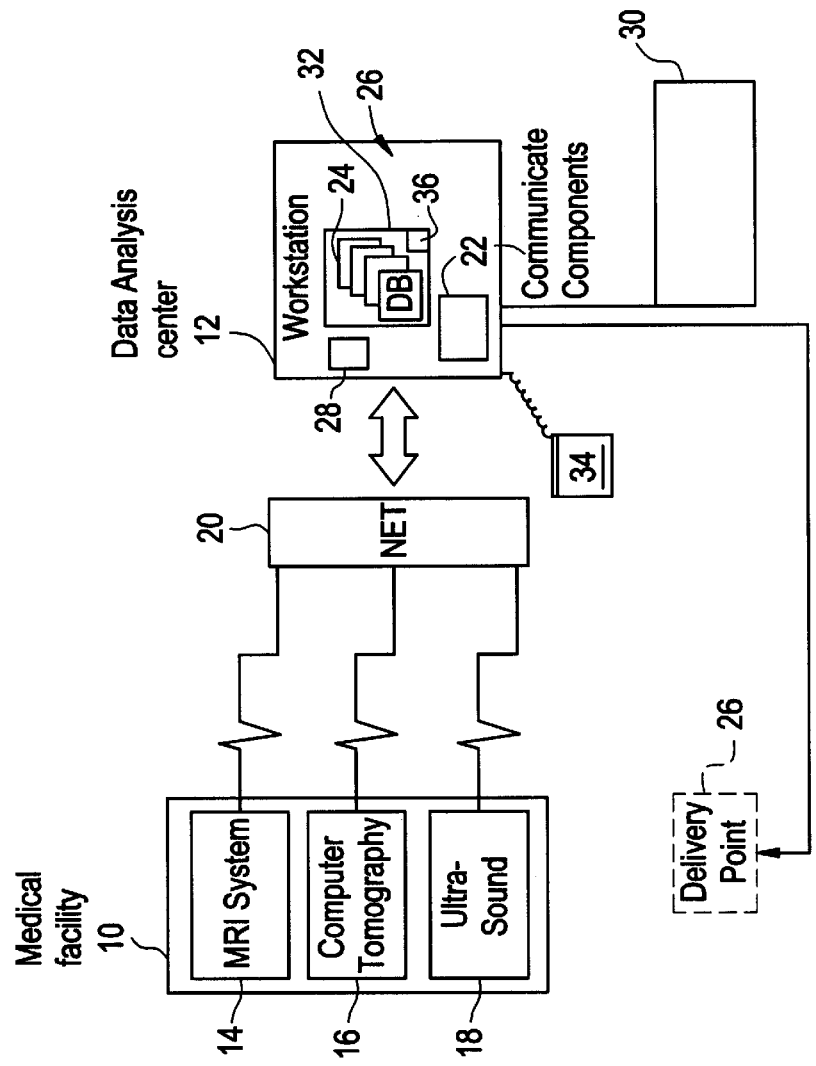
FIG. 1 is a block diagram of an exemplary medical facility operably connected with a workstation in accordance with the present technique.

Turning now to the drawings, and referring initially to FIG. 1, an exemplary medical facility and data processing system is illustrated. This particular medical facility 10 includes a plurality of scanners which provide medical imaging to a workstation 12. In one embodiment, the medical facility 10 includes an MRI system 14, a computed tomography system 16, and an ultrasound system 18. These and other modalities may be similarly communicated with the workstation 12, depending upon the capabilities of the medical facility 10, the types of diagnostic systems that generate a patient report, as well as other factors. In general, the present technique is particularly well suited to generating a customized patient report in conjunction with a wide variety of medical diagnostic system modalities including, but not limited to, MRI systems, CT systems, ultrasound systems, positron emission tomography (PET) systems, nuclear medicine systems, and so forth. The modalities (e.g., MRI system 14, CT system 16, ultrasound system 18) may be linked to the workstation 12 directly or via a remote access network 20. For remote access, any suitable network connection may be employed. Presently, advantageous network configurations may include both proprietary and dedicated networks as well as open networks, such as the Internet. Data may be exchanged between the various instruments in the medical facility 10 and the workstation 12 in any suitable format, such as in accordance with Internet protocol, the transmission control protocol, or other known protocols. Moreover, certain of the data may be transmitted or formatted via markup languages such as hyper-text markup language (HTML), or the extensible markup language (XML), or other standard languages.

The workstation 12 includes I/0 communication components 22 configured to receive the communications from the medical facility 10. The communications components 22 are linked to one or more databases 24. The databases 24 may include information on operating parameters, patient histories, and so forth, which are reserved for specific scanners as well as perhaps external populations of diagnostic equipment. Workstation 12 further includes a central processing unit (CPU) shown generally at 26, a random access memory (RAM) 28, an output device 30, for example a monitor, a mass storage device 32, and an input device 34, for example a keyboard. Workstation 12 may be a single user system, for example, a microcomputer, or a multi-user system. Additionally, workstation 12 may include multiple input devices 20, i.e., a keyboard, a mouse, or various automated data input devices, i.e., an optical scanner (not shown). An application program 36 is stored in mass storage device 32 and is executed by workstation 12. After receiving information from a scanner and processing the data, a patient report is generated by workstation 12 indicative of the diagnostic image scanning and patient attributes input to workstation 12. The patient report is then printed and hand delivered or sent to a designated delivery point 26. The delivery point 26 may be within the medical facility 10 or located remotely. The reports may be delivered by any specified means such as over the Internet, through e-mail, by fax, by mail, and so forth. The patient report is a customized diagnostic report as a result of the attributes input via input devices 20 and medical imaging conducted by a scanner operably connected to workstation 12.

Figure 2:
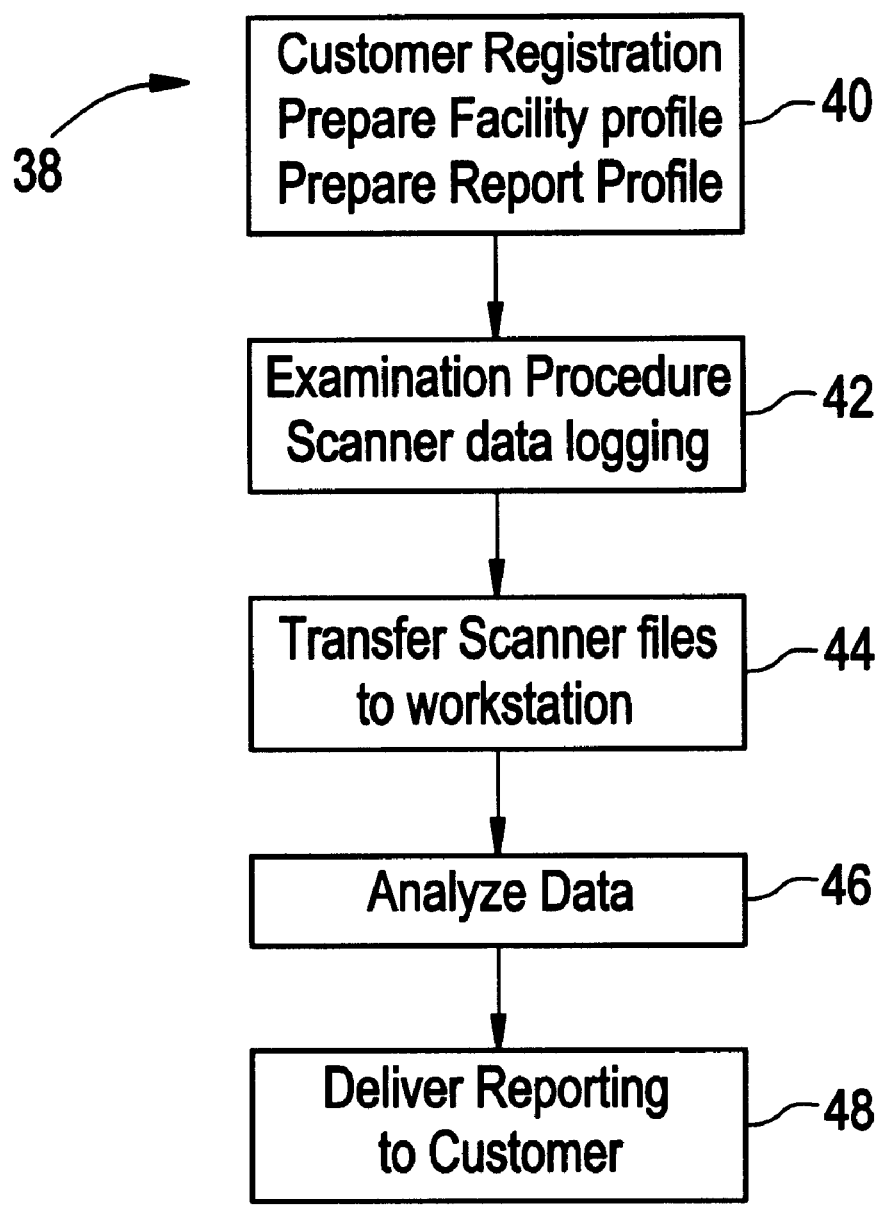
FIG. 2 is a flow chart illustrating an exemplary process flow in accordance with the present technique.

FIG. 2 illustrates a block diagram of an exemplary process flow incorporating the present technique as indicated generally at reference numeral 38. Initially, an end user or customer, such as an imaging technician or other medical personnel from a medical facility, will input a patient profile by inputting particular patient attributes via input devices 20, as in block 40. Among the preliminary tasks associated with the patient profile, the customer may input which scanner is selected within the medical facility as well as the attributes specific to the patient, such as age, gender, and any relevant medical history pertaining to the diagnostic screening/procedure. Further, the customer may complete a Report Profile which will be used by medical personnel (i.e., medical doctor) to determine the type of report and the format of the report. Once the profiles have been stored in workstation 12, one or more databases are configured to store and maintain the data necessary for preparing each report. Data may be archived to create historical databases which may be used for later comparisons with future screenings/procedures. After the profiles are established, they are used to generate customized patient report formats for each patient. The report will be generated using this format which is stored in the database under each patient.

The examination procedure is generally indicated by block 42. During the examination procedure, a patient undergoes an imaging procedure, such as an MRI or CT procedure for instance. During an examination, both the MRI and CT operating software generates and saves files containing examination information such as imaging setup parameters, examination codes, and date stamps to be used in preparing reports generated by the workstation. Each scanner preferably has a disk management strategy which is configured to retain data files -until they are transferred to the workstation.

Once the preliminary registration and linking is performed to establish a communication link between a scanner and the workstation, examination data logs are automatically transferred periodically to the workstation as indicated at block 44. The frequency of this transfer may be selected or altered to avoid overflow of the scanner data storage media. The transfer software may be configured to establish expected arrival frequency for each scanner and send an alert to appropriate personnel when a scanner appears to have dropped offline.

Next, the data received from the scanners is analyzed, as indicated by block 46 and further discussed with reference to FIGS. 3 and 4. The analysis process facilitates appropriation of the patient report in accordance with the Report Profile established for each patient and generates a customized diagnostic report tailored to that specific patient. A specific Report Profile may require that the examination data be analyzed and correlated with data from other scanners or other facilities. The results are displayed in a variety of formats including a scanned image and word text, for instance, as specified in each patient Report Profile.

Once the data is analyzed and the reports are prepared, the reports are generated for the customer, as indicated by block 48. The reports are delivered in a predetermined format specified in the Report Profile. The patient will then receive a patient specific report as a hand-delivered or mailed hard-copy, a fax, static pages that maybe viewed through an Internet browser, or any other mutually acceptable format.

A rules-based patient reporting system and method is implemented in an exemplary embodiment by software including the main operating program allowing end users the ability to easily design, customize, and modify patient reports. The compiled programs operate on the MS-DOS.™. 6.0 operating system and higher versions available from MICROSOFT Corporation, and use a graphic user interface (GUT) such as MICROSOFT WINDOWS. 3.1 for entering data and icon selected commands.

In one embodiment, the input device 34 may include a keyboard and a mouse for use in the WINDOWS environment, and the input device 34 may also include a data reading device such as a disk drive for importing and receiving patient information or attributes as well as previously stored patient and diagnostic information from storage media such as a floppy disk.

Outputs such as the graphic representation of the diagnostic imaging and patient information are sent to output device 30 such as a display for displaying the graphic representation of the scanned images aid corresponding patient information, as well as for use with the graphic user interface; for example, the WINDOWS environment. The capability for generating hardcopy printouts of such diagnostic and patient information, and the like is also provided in an exemplary embodiment for the patient to review. Alternatively, output device 30 may include specialized graphics programs to convert the generated graphic representation of diagnostic and patient information to a displayed graphic and/or to hardcopy plots such as bar charts and pie charts.

Figure 4:
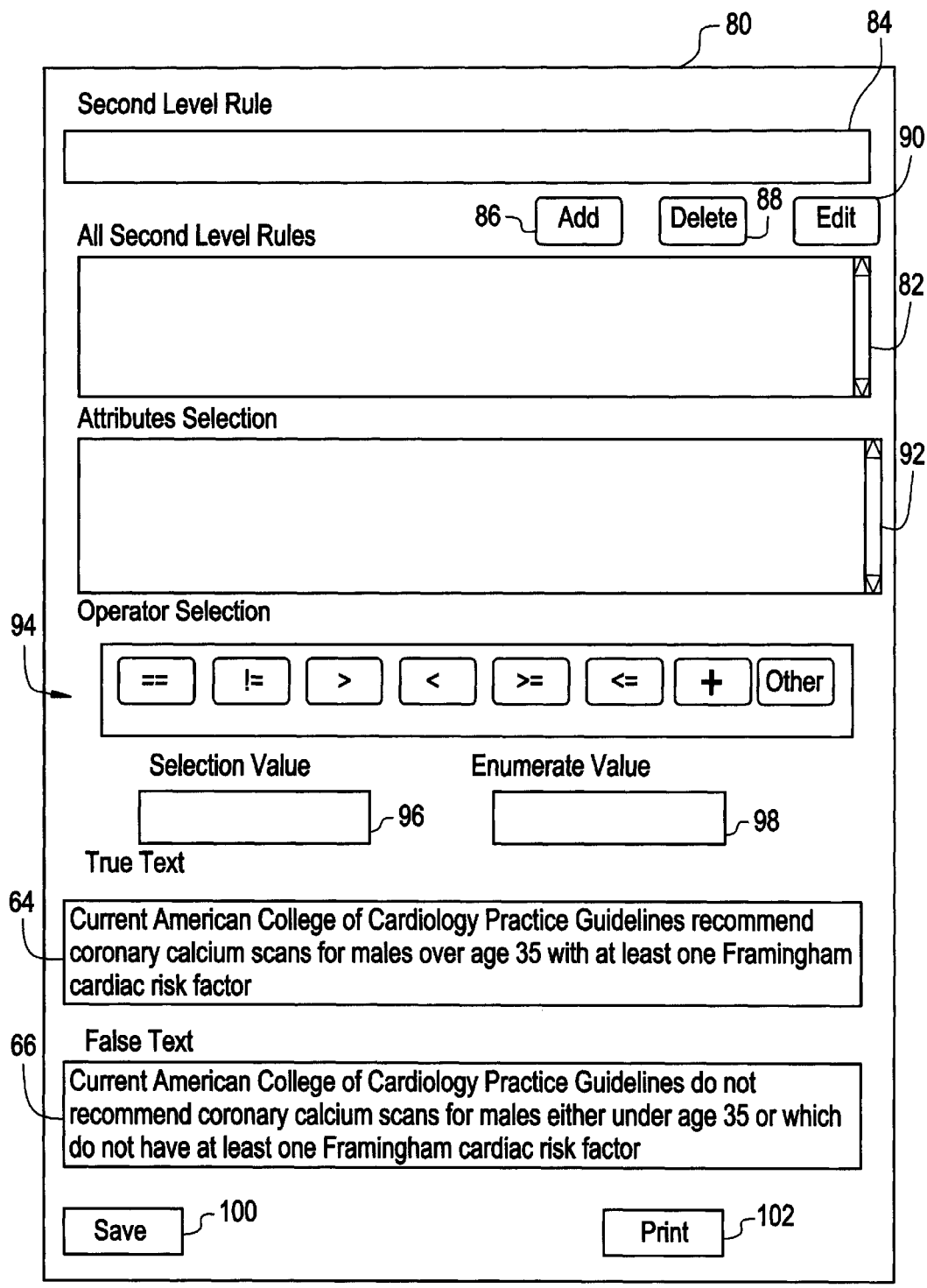
FIG. 4 is a continued screenshot of the exemplary user interface depicted in FIG. 3.

After the main operating program is installed and stored in workstation 12, a top level rule menu screen 50 is illustrated in FIG. 4 allowing the user to select program modules entitled ATTRIBUTES, RULES, ADD, DELETE, EDIT, or to exit from the operating program. By selecting the program modules, the user may access user input windows, pop-up or pull-down menus, and the like.

By selecting an ATTRIBUTE module, the operating program generates an attribute menu 54 or toolbar on a blank screen, as shown in FIG. 4. In an exemplary embodiment, an attribute is selected as indicative of any relevant patient information or diagnostic test result. Once an attribute is highlighted in attribute menu 54, a patient's gender for example, may be indicated by selecting a TRUE button 54 or a FALSE button 56. Alternatively, a drop down menu 58 may be employed to select the patient's gender or select a specific attribute corresponding to the attribute selected in attribute menu 54.

In an exemplary embodiment, a plurality of generic or spare attribute buttons 60 are provided for adding additional attributes to attribute menu 54 by an end user. Although three attribute buttons 60 are illustrated in FIG. 3, buttons for all attributes and spares may be accessed by selecting EDIT button 62 when a selected attribute is highlighted for selection in attribute menu 54.

Top level menu screen 50 further includes a Rule module for selecting a rule indicative of a series of end user defined Boolean logic tests using the attributes as variables to return either a TRUE RULE TEXT 64 or a FALSE RULE TEXT 66. (See FIG. 4). For example, a rule is selected from a top level rule menu 70, the selected rule is illustrated in a selected rule text box 72 indicative of the Boolean logic test between attributes of the selected rule. As an example, the rule selected in text box 72 queries a true or false condition as it relates to a diagnostic CT scan for coronary calcification scoring. More specifically, the Boolean logic test seeks a true or false condition if the patient's age is greater than thirty-five and the patient is a male and has a number of risk factors greater than one and the scan type is a coronary calcium scan. If the condition is true, then the TRUE TEXT in text box 64 will be generated. If the condition is false, then the FALSE TEXT in text box 66 will be generated. A selected attribute or top level rule may be edited, deleted, or added selecting corresponding buttons EDIT 62, DELETE 76, or ADD 78, respectively.

Figure 3:
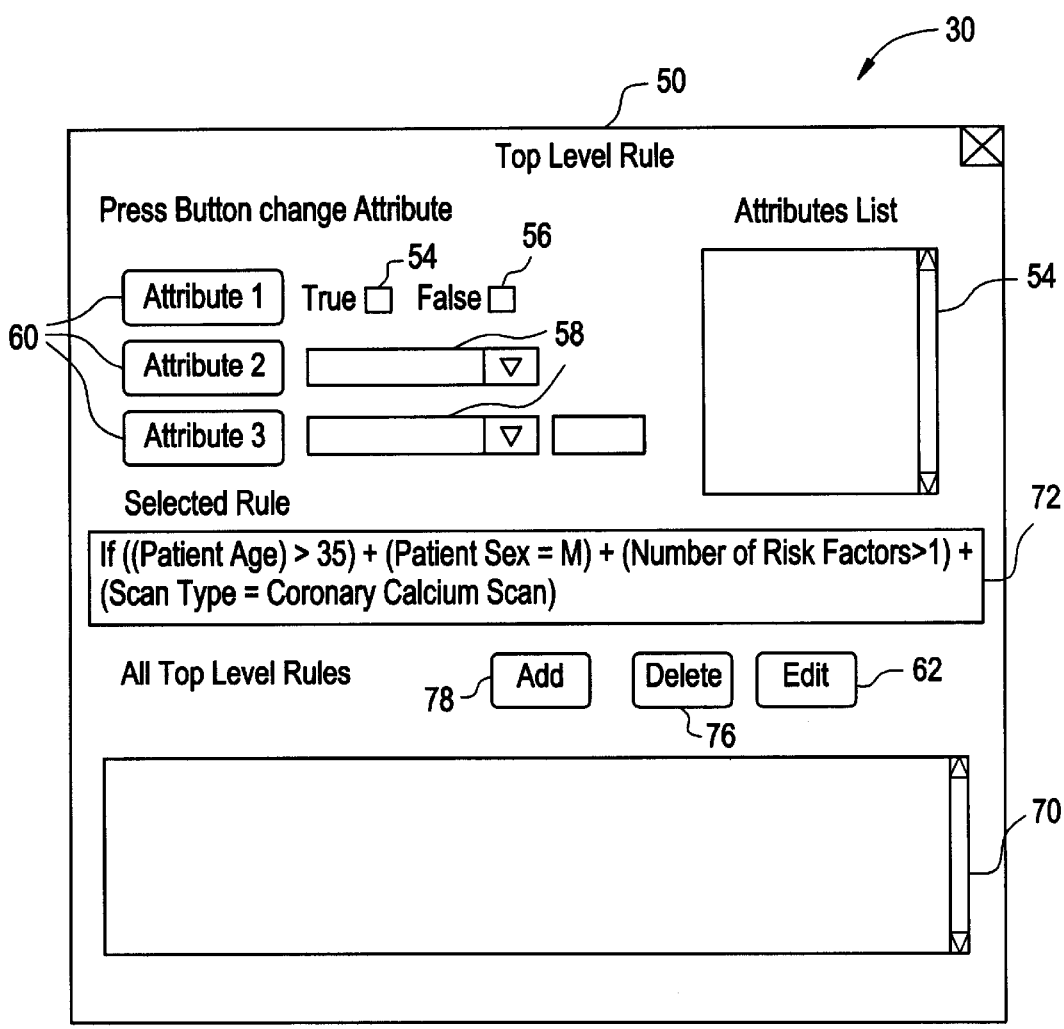
FIG. 3 is a screenshot of an exemplary user interface of the workstation of FIG. 1.

Referring now to FIG. 4, another screen shot 80 is illustrated that may be a separate page or a continuation of top level menu 50 in FIG. 3. Screen shot 80 illustrates a second level menu 82 that may be employed in conjunction with a selected top level rule to extend the hierarchy of a selected rule before generating text in text boxes 64 or 66. As with a selected top level rule, a selected or highlighted rule from menu 82 is depicted in a Boolean logic test form in a second level rule text box 84. A second set of ADD, DELETE, and EDIT buttons 86, 88, and 90, respectively, are included for adding, deleting, and editing a selected second level rule. A second attributes menu 92 is further included for use with a selected second level rule. It will be recognized that buttons 86, 88, and 90 may be employed for use with second attributes menu 92 as well.

Operator selection buttons are generally shown at 94 for use in editing or adding a top level rule and a second level rule. In an exemplary embodiment, buttons for basic Boolean logic operators are included for use in establishing a top or second level rule in boxes 72 and 84. For example, in one embodiment, Boolean logic qualifiers include: if, and, or, not, nor, greater than, greater than or equal to, less than, less than or equal to, equal to, not equal to, and the like. A selection value box 96 and an enumerate value box 98 are included for selecting or enumerating a value corresponding to a selected operator button 94.

Other commands such as saving an attribute or rule, or printing a patient report are accomplished by selecting the appropriate SAVE or PRINT buttons 100, 102, respectively.

Once the attributes and rules are selected, workstation 12 prepares a customized rule-based patient report. In one embodiment, a hard-copy patient report is generated that is in a format that is easily reviewed and digested by the patient. The patient report is preferably stored in the facility history database and is used for preparing reports and possibly providing historical data for comparison to future scanner files.

After the patient report rule-based format is selected by an end user (e.g., a physician) for meaningful patient review, reports can be generated based on Reporting Profiles, as previously discussed. The examination data may be parsed into groups or subgroups as required by the report profile for each patient and may generate current diagnostic medical status, such as current coronary calcification score, specific patient risk factors, and so forth. The results may be displayed in a variety of formats including time series, pie charts, and bar charts as determined by the patient's Report Profile. For example, in the case of an asymptomatic/mildly-affected patient, the screening application aims to catch the disease early and make the patient aware of what action should be taken, if any, to avert further damage. In the case of a symptomatic patient with some history of CVD risk, the customized patient report informs the patient of a current status, or if necessary, directs the patient to seek further medical advice.

The customized patient report configured by the end-user is a revolutionary idea, which can make the patient report more patient focused and better serving the patient by providing a message that advises him/her of a current medical condition and further actions to be taken, if any. The customized patient report may guide a patient into an improved lifestyle or direct the patient to a cardiologist/ physician who may take continue to provide medical care. The customized medical report also provides both the physician and the patient with an overall picture of the patient's health by presenting it in a quickly digestible format. Furthermore, it will be understood by one skilled in the pertinent art that the invention is not limited to calcium scoring as described herein for example, as it may apply to other emerging screening applications as well.

The patient report may also provide certain other information aside from the diagnostic rule-based reporting. Workstation 12 may generate heuristical reports based on current medical patient trends. The heuristical report generation is in an intelligent interpretation which reports statistics and detects trends and comparisons that are both practically and statistically significant. Heuristics may be used to select which features might be of interest to the patient based on his Report Profile and additional text and graphics may be automatically generated in addition to the patient's report to display these particular observations.

The above-described base functions comprise an ordered listing of executable instructions for implementing logical functions. The ordered listing can be embodied in any computer-readable medium for use by or in connection with a computer-based system that can retrieve the instructions and execute them. In the context of this application, the computer-readable medium can be any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CD ROM) (optical). It is even possible to use paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

Although the preceding embodiments are discussed with respect to medical imaging, it is understood that the image acquisition and processing methodology described herein is not limited to medical applications, but may be utilized in non-medical applications.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. An apparatus for generating a customized patient report comprising:

a memory for storing a plurality of patient specific attributes and a plurality of user defined rules, said attributes including patient specific medical image data;

a stored program configured to apply a rule to a corresponding attribute, said stored program configured to allow an end user to at least one of create, edit, and add at least one of said attributes and said user defined rules;

a processor operating with said stored program for processing to establish a conclusion to said rule; and an output device configured to generate the customized patient report having said conclusion in text format.

2. The apparatus of claim 1, wherein at least one of said plurality of user defined rules and said patient specific attributes are operably configurable using a graphical user interface.

3. The apparatus of claim 2, wherein said graphical user interface is configured to at least one of select, edit and add at least one of a user defined rule and an attribute and said conclusion in text format.

4. The apparatus of claim 1, wherein each user defined rule of said plurality of user defined rules is a operably configured allowing an end user to create at least one of a first logic test within said rule and a second logic test between rules.

5. The apparatus of claim 4, wherein said each user defined rule is configured to allow at least one of end user initial design and end user subsequent design.

6. The apparatus of claim 4, wherein said plurality of user defined rules are operably configured using Boolean logic tests.

7. The apparatus of claim 6, wherein said Boolean logic tests use corresponding attributes as variables to establish said conclusion.

8. The apparatus of claim 1, wherein said conclusion in text format is configurable by an end user.

9. The apparatus of claim 8, wherein the end user is one of a physician and medical personnel.

10. The apparatus of claim 1, wherein said conclusion in text format is selected as a result of a content box identified by said conclusion to said rule.

11. The apparatus of claim 10, wherein said content box is one of a True condition and a False condition each having corresponding text editable by an end user.

12. A customized patient reporting system comprising:

a medical facility comprising a plurality of medical imaging devices; and a workstation configured to receive medical imaging data from said medical imaging devices;

wherein said workstation includes a memory for storing a plurality of patient specific attributes and a plurality of user defined rules, said plurality of patient attributes includes said medical imaging data;

a stored program configured to apply a rule to a corresponding attribute, said stored program configured to allow an end user to at least one of create, edit, and add at least one of said attributes and said user defined rules;

a processor operating with said stored program for processing said rule to establish a conclusion to said rule; and an output device configured to generate a customized patient report having said conclusion in text format.

13. The reporting system of claim 12, wherein at least one of said user defined rules and said patient specific attributes are operably configurable using a graphical use interface.

14. The reporting system of claim 12, wherein said graphical user interface is configured to at least one of select, edit and add at least one of a user defined rule and an attribute.

15. The apparatus of claim 12, wherein each user defined rule of said plurality of user defined rules is a operably configured allowing an end user to create at least one of a first logic test within said rule and a second logic test between fines.

16. A method for generating a customized patient report comprising:

storing a plurality of patient specific attributes and a plurality of rules; said attributes include patient specific medical image data;

configuring a stored program to apply a rule of said plurality of rules to corresponding attributes, said stored program configured to allow an end user to at least one or create, edit, and add at least one of said attributes and said user defined rules;

processing said rule to establish a conclusion to said rule; and configuring an output device configured to generate the customized patient report having said conclusion in text format.

17. The method of claim 16, wherein at least one of said text format and said attributes and said rules are end-user editable.

18. The method of claim 16, wherein at least one of said user defined rules and said patient specific attributes and said text format are operably configurable using a graphical user interface.

19. The method of claim 18, wherein said graphical user interface is configured to at least one of select, edit and add at least one of a user defined rule and an attribute and text in sad text format.

20. The method of claim 16 further comprising:

configuring each user defined rule of said plurality of user defined rules to allow an end user to create at least one of a first logic test within said rule and a second logic test between rules.

21. The method of claim 20, wherein each of said plurality of user defined rules is operably configured using Boolean logic test.

22. The method of claim 21, wherein sad Boolean logic tests use corresponding attributes as variables to establish said conclusion.

23. A rule based patient diagnostic reporting method comprising:

inputting patient information including patient specific attributes and diagnostic test result, said attributes including patient specific medical image data;

configuring a stored program using a graphical user interface to establish in array of related and unrelated relationships between said patient information to identify which content block is inserted in a generated patient report said stored program configured to allow an end user to at least one of create, edit, and add at least one of said attributes and said relationships; and generating a customized patient report having a conclusion in text format.

24. The method of claim 23, wherein said diagnostic test results includes medical imaging data from at least one of a plurality of medical imaging devices.

25. The method of claim 24, wherein each said relationship of said array of related and unrelated relationships is a Boolean logic test comprising a user defined rule having at least one attribute as a variable therein.

26. The method of claim 25, wherein said graphical user interface is configured to at least one of select, edit and add at least one of said user defined rule and said attribute and said text format.

27. The method of claim 26 further comprising:

operably configuring each user defined rule of a plurality of user defined rules to allow an end user to create at least one of a first logic test within said each user defined rule and a second logic test between selected rules of said plurality of user defined rules.

28. The method of claim 27, wherein each of said plurality of user defined rules is operably configured using Boolean logic tests.

29. The method of claim 28, wherein said Boolean logic tests use corresponding attributes as variables to establish said conclusion.

30. A computer-readable medium storing computer instructions for:

storing a plurality of patient specific attributes and a plurality of rules, said attributes including patient specific medical image data;

configuring a stored program to apply a rule of said plurality of rules to corresponding attributes;

configuring said stored program to allow an end user to at least one of create, edit, and add at least one of said attributes and said user defined rules;

processing said rule to establish a conclusion to said rule; and configuring an output device to generate a customized patient report having said conclusion in text format.

31. A tangible medium for storing a computer program comprising:

instructions for storing a plurality of patient specific attributes and a plurality of rules, said attributes including patient specific medical image data;

instructions for configuring a stored program to apply a rule of said plurality of rules to corresponding attributes;

instructions for configuring said stored program to allow an end user to at least one of create, edit, and add at least one of said attributes and said user defined rules;

instructions for processing said rule to establish a conclusion to said rule; and instructions for configuring an output device to generate a customized patient report having said conclusion in text format.

* * * * *